United States Patent [19]
Olstein et al.

[11] Patent Number: 5,536,783
[45] Date of Patent: Jul. 16, 1996

[54] FLUORESCENT POLYMERS USEFUL IN CONJUNCTION WITH OPTICAL PH SENSORS

[75] Inventors: Alan Olstein, Mendota Heights; William Fowler, Minneapolis; Jo Pritchard, Mound, all of Minn.

[73] Assignee: Optical Sensors Incorporated, Minneapolis, Minn.

[21] Appl. No.: 453,633

[22] Filed: May 30, 1995

Related U.S. Application Data

[62] Division of Ser. No. 74,749, Jun. 10, 1993.

[51] Int. Cl.$^6$ .............................. C08F 8/30; C08L 75/00
[52] U.S. Cl. ..................... 525/129; 525/127; 525/130; 128/634; 385/12; 385/117; 528/65; 528/70; 422/82.07; 422/82.11; 422/82.08
[58] Field of Search ................... 525/127, 129, 525/130; 528/70, 65; 128/634; 385/12, 117; 422/82.07, 82.11, 82.08

[56] References Cited

U.S. PATENT DOCUMENTS

| | | | |
|---|---|---|---|
| 4,508,916 | 4/1985 | Newell et al. | 556/420 |
| 4,785,814 | 11/1988 | Kane | 128/634 |
| 4,816,130 | 3/1989 | Karakelle et al. | 204/403 |
| 4,842,783 | 6/1989 | Blaylock | 264/1.4 |
| 5,151,535 | 9/1992 | Fuchikami et al. | 554/220 |
| 5,166,990 | 11/1992 | Riccitelli | 385/12 |
| 5,277,872 | 1/1994 | Bankert et al. | 422/82.01 |
| 5,453,248 | 9/1995 | Olstein | 422/82.07 |

FOREIGN PATENT DOCUMENTS

| | | |
|---|---|---|
| 2132348 | 7/1984 | United Kingdom . |
| WO88/05533 | 7/1988 | WIPO . |
| WO90/00572 | 1/1990 | WIPO . |

OTHER PUBLICATIONS

H. J. Hageman et al., "Photoinitiators and Photocatalysts for Various Polymerisation and Crosslinking Processes," in *Radiation Curing of Polymers* II, ed. D. R. Randell (The Royal Society of Chemistry, 1991), at pp. 46–53.

*Primary Examiner*—W. Robinson H. Clark
*Attorney, Agent, or Firm*—Reed & Robins

[57] ABSTRACT

An optical sensor is provided for measuring the pH of a fluid sample. The sensor is formulated using a fluorescent polymer composition comprising a copolymer of a water-dispersable, polyether-containing urethane olefin precursor and a fluorescent monomer species, wherein the ratio of precursor and fluorescent monomer species is such that a predetermined apparent pKa is provided. The sensor is prepared by coating the distal end of an optical waveguide with the fluorescent polymer composition, and curing the copolymer contained in the composition, e.g., by exposure to radiation of a suitable wavelength.

13 Claims, 2 Drawing Sheets

FLUORESCENT POLYMERS USEFUL IN CONJUNCTION WITH OPTICAL PH SENSORS

This application is a divisional of U.S. application Ser. No. 08/074,749, filed Jun. 10, 1993.

TECHNICAL FIELD

The present invention relates generally to optical sensors for measuring the pH of a fluid, and more particularly relates to a novel optical sensor system containing a membrane of a fluorescent hydrophilic urethane copolymer. The invention additionally relates to fluorescent polymeric compositions for use in an optical pH sensor, and to membranes which may be manufactured therefrom. One important application of the invention involves the precise measurement of pH in the physiological range.

BACKGROUND

Chemical sensors are generally known for use in a wide variety of areas such as medicine, scientific research, industrial applications and the like. Fiber optic and electrochemical approaches are generally known for use in situations where it is desired to detect and/or measure the concentration of a parameter at a remote location without requiring electrical communication with the remote location. Structures, properties, functions and operational details of fiber optic chemical sensors can be found in U.S. Pat. No. 4,577,109 to Hirschreid, U.S. Pat. No. 4,785,814 to Kane, and U.S. Pat. No. 4,842,783 to Blaylock, as well as Seitz, "Chemical Sensors Based on Fiber Optics," *Analytical Chemistry*, Vol. 56, No. 1, January 1984, each of which is incorporated by reference herein.

Publications such as these generally illustrate that it is known to incorporate a chemical sensor into a fiber optic waveguide, an electrochemical gas sensor or the like, in a manner such that the chemical sensor will interact with the analyte. This interaction results in a change in optical properties, which change is probed and detected through the fiber optic waveguide or the like. These optical properties of chemical sensor compositions typically involve changes in colors or in color intensities. In these types of systems, it is possible to detect particularly minute changes in the parameter or parameters being monitored in order to thereby provide especially sensitive remote monitoring capabilities. Chemical sensor compositions that are incorporated at the distal end of fiber optic sensors are often configured as membranes that are secured at the distal tip end of the waveguide device or optrode.

Sensors of this general type are useful in monitoring the pH of a fluid, measuring gas concentrations such as oxygen and carbon dioxide, and the like. Ion concentrations can also be detected, such as potassium, sodium, calcium and metal ions.

A typical fiber optic pH sensor positions the sensor material at a generally distal location with the assistance of various different support means. Support means must be such as to permit interaction between the pH indicator and the substance being subjected to monitoring, measurement and/or detection. With certain arrangements, it is desirable to incorporate membrane components into these types of devices. Such membrane components must possess certain properties in order to be particularly advantageous. Many membrane materials have some advantageous properties but also have shortcomings. Generally speaking, the materials must be biocompatible, hemocompatible for use in the bloodstream, selectively permeable to hydrogen ions, and of sufficient strength to permit maneuvering of the device without concern about damage to the sensor.

It is also desirable to have these membrane materials be photocurable (such that curing is neater, can be done more rapidly, on a smaller scale, and directly on the optical fiber), resistant to shear forces (e.g., as present in a bloodstream), and compatible with different substrates, such that there is a choice of fiber optic materials which can be used to fabricate the sensor. It is also preferred, clearly, that a signal of sufficient intensity be produced, such that measurement is as accurate as is reasonably possible. The optical pH sensors which are currently available are frequently inadequate with regard to one or more of the aforementioned criteria.

It is additionally desired that the materials used for the sensor membrane be constructed such that pH values in a relatively wide range may be accurately measured. To date, this has not been the case with optical pH sensors. Rather, indicator compositions of prior art optical sensors typically display an apparent pKa which is substantially lower than is desirable for the accurate and precise measurement of a pH above about 7.0, e.g., as is true for the physiological pH range.

The present invention is addressed to novel fluorescent copolymer compositions which have been found to be particularly suitable for use as membranes and membrane-like components in an optical pH sensor and which provide for optical sensors which meet each of the above-mentioned criteria. That is, optical sensors as provided herein tend to adhere well to different types of substrates, eliminating in some cases the need to silanize the substrate surface, provide for superior signal intensity, are quite hemocompatible relative to prior art compositions, are rapidly cured with light, and are resistant to shear forces such as those present in flowing blood. Additionally, the novel polymer compositions are such that their apparent pKa may be raised or lowered at will, enabling measurement of a wide range of pH values in a fluid sample. It is preferred that the apparent pKa of the compositions be in the range of approximately 6.6 to 8.0, more preferably in the range of approximately 7.2 to 7.8, most preferably in the range of approximately 7.2 to 7.4, such that pH values in the physiological range may be precisely determined.

OVERVIEW OF RELATED ART

The following references relate to one or more aspects of the present invention:

U.S. Pat. No. 4,785,814 to Kane describes an optical probe useful for measuring pH and oxygen and blood. The device includes a membrane constructed of a hydrophilic porous material containing a pH-sensitive dye.

U.S. Pat. No. 4,842,783 to Blaylock describes a fiber optic chemical sensor which, at the distal end of the optical fiber, is provided with a photocrosslinked polymeric gel having a dye adsorbed therein.

PCT Publication No. WO88/05533, inventors Klainer et al., describes a fiber optic sensing device for measuring a chemical or physiological parameter of a body fluid or tissue, in which a polymer containing photoactive moieties is directly bound to the fiber optic tip.

PCT Publication No. WO90/00572, inventors Boesterling et al., describe the use of a urethane or an acrylamide hydrogel for measuring pH and/or $pCO_2$ in a fluid. The hydrogels are prepared by reacting an isocyanate prepolymer with a derivatized azo dye, i.e., an absorbance dye which is a molecule containing either an amino or hydroxyl functionality.

H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 46–53, identify a number of materials which will act to catalyze radiation curing of multifunctional monomers or oligomers.

SUMMARY OF THE INVENTION

Accordingly, it is a primary object of the invention to address the above-mentioned needs in the art, by providing an optical sensor for measuring the pH of a fluid, which sensor gives rise to the numerous advantages identified above.

It is another object of the invention to address these needs by providing a fluorescent polymer composition for incorporation into such an optical sensor, wherein the fluorescent polymer composition comprises a copolymer of a water-dispersable, polyether-containing urethane olefin precursor and a copolymerizable monomeric fluorescent indicator species.

It is still another object of the invention to provide a membrane fabricated from the aforementioned fluorescent polymer composition.

It is yet another object of the invention to provide a method for making an optical sensor containing the aforementioned fluorescent composition by copolymerizing the water-dispersable, polyether-containing urethane olefin precursor and the copolymerizable monomeric fluorescent indicator species on the fiber optic tip.

It is a further object of the invention to provide such a method which involves irradiating the precursor and the copolymerizable monomeric fluorescent indicator species through the fiber.

Additional objects, advantages and novel features of the invention will be set forth in part in the description which follows, and in part will become apparent to those skilled in the art upon examination of the following, or may be learned by practice of the invention.

In one aspect, then, a fluorescent polymer composition is provided which is useful in an optical sensor for the measurement of pH in a fluid sample. The fluorescent polymer composition comprises a copolymer of (a) a water-dispersable, polyether-containing urethane olefin precursor, and (b) a monomeric fluorescent indicator species. The ratio of the urethane olefin precursor to the fluorescent species is calculated so as to provide the composition with a predetermined apparent pKa. Generally, it is preferred that the ratio be such that the apparent pKa of the composition is in the range of about 6.6 to 8.0, more preferably in the range of about 7.2 to 7.8, most preferably in the range of about 7.2 to 7.4, which in turn optimizes the composition for use in measuring pH in the physiological range.

In another aspect, a cross-linked, selectively permeable (i.e., $H^+$-permeable) membrane is provided which is useful for fabricating an optical pH sensor. The membrane comprises a polymeric matrix of the novel fluorescent composition.

In still another aspect, an optical sensor is provided for the measurement of pH in a fluid sample, comprising an optical waveguide to receive light from a light source, and a pH-sensitive medium disposed on the waveguide which fluoresces in response to light from the light source, wherein the intensity of fluorescence is dependent on the pH of the environment being monitored, and the pH-sensitive medium comprises the aforementioned fluorescent polymer composition. The pH-sensitive medium may or may not be present in the form of a membrane.

Still other aspects of the invention, as noted above, involve methods for making and using the novel optical sensors.

BRIEF DESCRIPTION OF THE DRAWING

In the course of this description, reference will be made to the attached drawings, wherein.

DETAILED DESCRIPTION OF THE INVENTION

Figure 1:
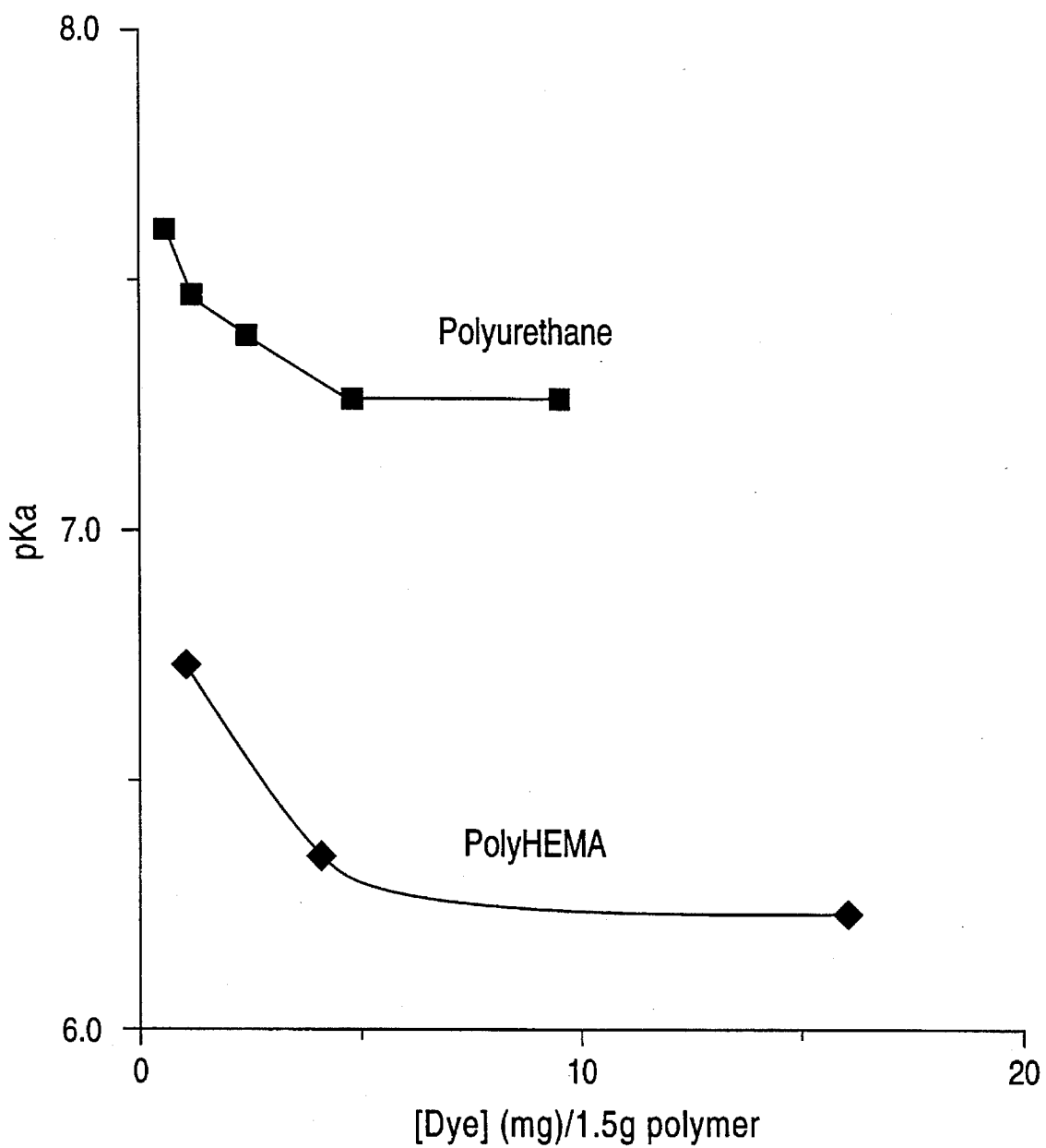
FIG. 1 is a graph illustrating the effect of polymer used on pKa, for hydroxyethylmethacrylate- and for the polyurethane-based fluorescent composition of the invention.

Before the present compositions, membranes, sensors and methods of manufacture are disclosed and described, it is to be understood that this invention is not limited to specific sensor formats, specific membrane compositions, or particular curing processes, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a water-dispersable, polyether-containing urethane olefin precursor" includes mixtures of such precursors, reference to "a fluorescent indicator species" includes mixtures of two or more such indicator species, and the like.

In describing and claiming the present invention, the following terminology will be used in accordance with the definitions set out below.

The term "polymer" as used herein is intended to include both oligomeric and polymeric materials, i.e., compounds which include two or more monomeric units. The term is also intended to include "copolymeric" materials, i.e., containing two or more different monomeric units.

The term "urethane" is used herein in its conventional sense to denote organic compounds containing a recurring -O-(CO)-NH- linkage. The term "polyether-containing urethane" is intended to mean a polymer containing recurring urethane units as just defined, as well as recurring ether linkages $[-(CH_2)_n-O-]$ where n is an integer greater than 1, typically in the range of 1 to 6, inclusive, most typically 1, 2 or 3.

The term "olefin" is used in its conventional sense to mean a molecular entity containing a double bond; the preferred olefinic species of the invention are molecular entities containing at least one terminus represented by the general formula $-R-(CO)-CR'=CH_2$, wherein R is O or NH, and R' is H or lower alkyl. Although such olefinic termini are preferred, it will be appreciated by those skilled in the art that other olefinic termini may be substituted therefor.

The term "precursor" is used herein to mean a compound which when polymerized, copolymerized and/or cross-linked will give rise to a desired polymer.

The term "water-dispersable" as used herein is intended to mean compatible with water or with aqueous solutions. Typically, water uptake by cured films of the "water-dispersable" precursor used to form the fluorescent copolymer will be at least about 10% by weight, more preferably at least about 20% by weight, and most preferably at least about 35% by weight.

In describing chemical compounds herein, the term "lower alkyl" is used in its conventional sense to mean an alkyl group of 1 to 6 carbon atoms, e.g., methyl, ethyl, n-propyl, isopropyl, n-butyl, isobutyl, t-butyl, and the like.

The fluorescent polymer composition which serves as the sensing means for the measurement of pH, as noted above, comprises a copolymer of a water-dispersable, polyether-containing urethane olefin precursor and a copolymerizable fluorescent monomer species. The preferred molecular weight of the copolymer is in the range of approximately 1000 to 25,000, more preferably in the range of approximately 1800 to 5000, and most preferably in the range of approximately 1800 to 2500. The urethane olefin precursor contains recurring urethane units, recurring ether linkages, and olefinic termini represented by the general formula -R-(CO)-CR'=CH$_2$, wherein R and R' are as defined earlier; it should also be noted that the R and R' at the different termini are not necessarily the same (i.e., R may be O at one terminus and NH at the other, and, similarly, R' may be H at one terminus and CH$_3$ at another). Preferred urethane olefin precursors are represented by the general structural formula

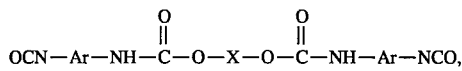

wherein X is as defined above, to urethane olefin precursors by replacing the terminal isocyanate moieties with olefin termini. The isocyanate-terminated starting material is reacted with the desired olefin monomer or oligomer, i.e., a hydroxy- or amine-terminated acrylate, methacrylate, acrylamide, methacrylamide, e.g., hydroxyethylmethacrylate (in which case n=2). Urethane precursors are commercially available from W. R. Grace & Co. (Lexington, Mass.), and Miles Laboratories, Inc. (Pittsburgh, Pa.). Urethane olefin precursors such as 9454, 9455, 9734 and 9467, and RCC-12-893, Photomers 6230 and 6264 are commercially available from Monomer-Polymer and Dajec Laboratories, Inc. (Trevose, Pa.) and Henkel Corporation (Ambler, Pa.), respectively.

The copolymerizable fluorescent monomer species may be virtually any fluorescent dye or material which is sensitive to pH, modified so as to enable copolymerization with the urethane olefin precursor. Exemplary preferred modifications include incorporation into the fluorescent monomer species of a reactive moiety such as acrylate, acrylamide, allyl esters, allyl amides, and the like, such that the fluorescent species is thereby incorporated into the backbone of the polymer chain. Examples of fluorescent monomer species useful herein include fluorescein and fluorescein derivatives such as carboxyfluorescein, fluorescein acrylamide, fluorescein isothiocyanate, coumarin, seminaphthorhodafluorescein, seminaphthofluorescein, naphthofluorescein, hydroxypyrene trisulfonic acid and dichlorofluorescein, and the like, again, bearing a reactive site effective to promote incorporation into the copolymer.

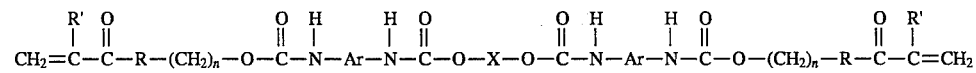

wherein: R and R' are as defined previously; n is typically in the range of 1 to about 6; Ar is a monocyclic aromatic moiety, preferably phenyl, either unsubstituted or substituted with one to four substituents which are selected so as not to interfere with polymerization or use of the cured polymer in the pH sensor, e.g., lower alkyl, halogen, nitro and the like; and X is a polyether linkage containing approximately 2 to 100, preferably 10 to 50, most preferably 15 to 25, recurring mer units having the structure [-(CH$_2$)$_n$-O-] where n is an integer of 1 or more, typically 1 to 6, more typically 2 or 3, i.e., (-CH$_2$-CH$_2$-O-), (-CH$_2$-CH$_2$-CH$_2$-O-), or combinations thereof. These polyether linkages may be further substituted with an additional -CO-NH-Ar-NH-CO$_2$-(CH$_2$)$_n$-R-(CO)-CR'=CH$_2$ group to provide a trifunctional urethane olefin precursor. Methods for synthesizing urethane olefin precursors are described in detail in commonly assigned, copending U.S. patent application Ser. No. 07/911,175, entitled "Cross-Linked Gas Permeable Membrane of a Cured Perfluorinated Urethane Polymer, and Optical Gas Sensors Fabricated Therewith," filed 12 Aug. 1992, the contents of which are hereby incorporated by reference. Briefly, that method involves conversion of isocyanate-terminated compounds represented by the general formula An important advantage of the invention is the capability of adjusting the apparent pKa of the resultant fluorescent polymer composition by varying the ratio of polymerizable fluorescent indicator species to urethane acrylate precursor in the copolymer. The tuning of the apparent pKa in this way gives rise to an indicator which generates a maximal signal change in the desired pH range. An example of this is the use of fluorescein dyes which have a published pKa of 6.5. By varying the ratio of such fluorescein dye monomers the apparent pKa in the resultant polymer system is in the range of about 7.2 to 7.8. That is, the maximally emissive form of the dye, the dianion, undergoes ionization in the physiological range, pH 7.2 to 7.8, rather than a full pH unit lower. The fluorescent polymer then becomes far more fluorescent in the desired pH range, giving maximum sensitivity in the physiological range. A lower apparent pKa can be achieved in this system by varying the amount and nature of additional comonomers. To achieve a pKa in the range of about 7.2 to 7.8 the ratio of polymerizable fluorescent comonomer to polyether-containing urethane species, in equivalents, should be in the range of about 0.001 to about 0.100, more preferably in the range of about 0.005 to about 0.015.

The optical sensors of the invention are typically prepared by first making a coating solution of the water-dispersable urethane olefin precursor and the copolymerizable monomeric species. The coating solution is prepared by admixing the urethane olefin precursor, the photoinitiator and the fluorescent monomer species, modified as described above, in a suitable solvent. The total amount of the dissolved solids is typically in the range of about 50% to 75% by weight. Generally, the coating solution will contain on the order of 35 to 90 g urethane olefin precursor, $1 \times 10^{-3}$ to $5 \times 10^{-2}$ g photoinitiator, and $5 \times 10^{-4}$ to $5 \times 10^{-2}$ g fluorescent monomer per 100 g solution. (It may be noted from the aforementioned preferred ranges that the ratio of dye to polymer, in equivalents, is in the range of about 0.001 to 0.100, more preferably in the range of about 0.005 to about 0.015.) Preferred solvents include water-miscible, low boiling point solvents such as methanol and ethanol, and partially water-miscible solvents such as ethyl acetate. A particularly preferred low boiling point solvent is 40% ethanol in water. However, water-miscible, polar solvents that have higher boiling points may also be used, such as dimethylsulfoxide, dimethylformamide, N-methylpyrrolidone, dimethylacetamide, or the like. A preferred high boiling point solvent is dimethylsulfoxide used at about 25% by weight.

The coating solution is applied to the distal end of an optical fiber by coating, painting, dipping, or the like, and then cured on the fiber. Alternatively, the copolymer may be cured first and then affixed to the fiber optic tip. However, the former method is preferred. To cross-link the urethane olefin precursor, a cross-linking agent may be dissolved in the coating solution. The cross-linking agent may be any di- or multifunctional acrylate. Examples of such cross-linking agents include

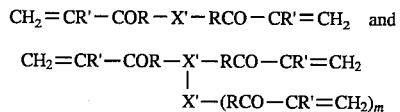

$$CH_2=CR'-COR-X'-RCO-CR'=CH_2 \text{ and}$$

$$CH_2=CR'-COR-X'-RCO-CR'=CH_2$$
$$|$$
$$X'-(RCO-CR'=CH_2)_m$$

wherein R and R' are as defined above, m is 1, 2 or 3, and X' is a polyether substituent as defined above or a hydrocarbon, preferably alkylene, group containing about 2 to 20 carbon atoms.

Curing may be carried out by exposing the aforementioned solution, preferably in the form of a coating on the fiber optic tip, to radiation of a wavelength effective to initiate copolymerization. In a particularly preferred embodiment, curing is carried out on the fiber substrate using radiation transmitted through the fiber, i.e., after a solution containing the urethane olefin precursor and the fluorescent monomeric species has been provided on the fiber tip by coating, painting, dipping, or the like. Alternatively, as alluded to above, the fluorescent polymer composition may be cured to form a cross-linked membrane, which is then deposited on the surface of the optical fiber. With glass fibers, it has typically been necessary to prime the fiber surface prior to photopolymerization or deposition of the sensing membrane thereonto. An example of a suitable glass primer is γ-methacryloxypropyl trimethoxysilane. Once cured, the sensor thus formed may be cleaned of residual unreacted monomer by soaking in an innocuous solvent such as dimethylsulfoxide or water.

As an alternative to photocuring, some systems may be curable upon exposure to heat, preferably using temperatures in the range of about 40° C. to about 100° C. and a thermal initiator, e.g., a peroxide or a vinyl polymerization initiator such as that available under the name Vazo® from E.I. DuPont de Nemours & Co., Wilmington, Del.

When curing is effected using radiation, it is necessary to carry out the curing step in the presence of a photoinitiator. Suitable photoinitiators are radical photoinitiators that are well known to those skilled in the art. Examples of such photoinitiators include α-alkoxy deoxybenzoins, α,α-dialkoxy deoxybenzoins, α,α-dialkoxy acetophenones, 2-hydroxy-2,2-dialkyl acetophenones, benzophenones, thioxanthones, benzils, and other compounds identified by H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 46–53, cited supra. The disclosure of the aforementioned reference is incorporated by reference herein.

Figure 2:
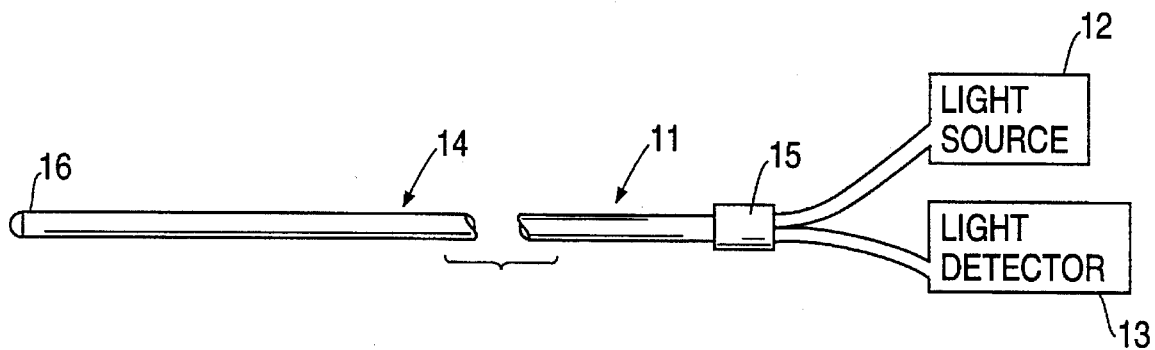
FIG. 2 is a generally schematic view of a chemical sensor device according to the present invention as incorporated in a fiber optic pH sensor device.
Figure 3:
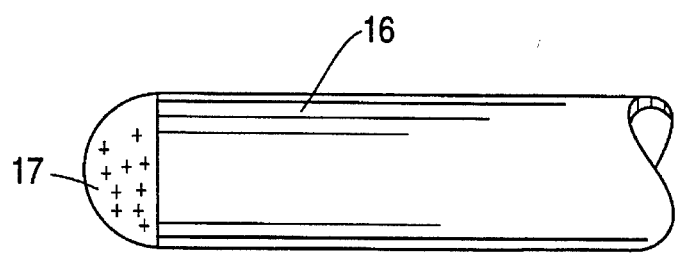
FIG. 3 is an enlarged, detail and generally schematic view of the distal end portion of a sensor device generally in accordance with FIG. 2.

FIGS. 2 and 3 show a typical fiber optic pH sensor arrangement. The illustrated device 11 includes a light source 12 for directing probe radiation into the device, as well as a light detector 13 for sensing and detecting radiation from the device. Device 11 includes one or more optical fibers 14 that are joined to light source 123 and to light detector 13 through a suitable junction assembly 15 at a location which is proximal of the distal end portion 16 of the optical fiber 14. As is generally known, each optical fiber 14 includes a core surrounded by a cladding or covering.

Distal end portion 16 has a distal tip 17 which is a membrane of a copolymer of a water-dispersable, polyether-containing urethane olefin precursor and a copolymerizable fluorescent monomer species. The fluorescent monomer species enables the membrane to undergo a known change in color, color intensity or other property, which change is observed by the light detector 13 in a manner generally known in the art.

Examples of suitable fiber substrate materials include glass, plastic, glass/glass composite and glass/plastic composite fiber waveguides. A critical characteristic of optical fibers is attenuation of the optical signal. Thus, glasses which contain unacceptable levels of transition-metal impurities when prepared from naturally occurring materials lead to high absorption losses. High silica fibers of acceptable quality can be prepared from purified starting materials (e.g., silicon tetrachloride and germanium tetrachloride) using conventional glass-melting techniques of melting, fining and drawing into fibers. In order to promote adhesion of the membrane to the fiber, the surface of the tip of the fiber substrate may be silanized, such as with γ-methacryloxypropyl trimethoxysilane as primer, as discussed above.

As noted earlier, the primary utility of the present invention is in the detection and measurement of pH. However, the membrane and sensor of the invention may also be used in a variety of other contexts, e.g., in detecting and/or quantitating $O_2$ and $CO_2$, for on-line sensing in a flowing fluid stream, or in static application.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE 1

Synthesis of Polyurethanemethacrylamide, a Hydrophilic Urethane Olefin Prepolymer Using a clean, dry, metal spatula, 18.39 g (0.0287 equivalents) Hypol® 2000 (W. R. Grace & Co., Lexington, Mass.), a hydrophilic prepolymer, was transferred from its storage container, which had been purged with argon during and for two minutes after the transfer, to a 50 ml flame-dried reaction kettle. Recrystallized N-(2-hydroxypropyl)methacrylamide (HPMA) (4.11 g; 0.0287 equivalents)

(Polyscience Corp., Warrington, Pa.) was rapidly added to the reaction kettle and, immediately thereafter, the kettle was purged with argon after replacing and securely clamping the lid in place. An air-driven stirrer equipped with a glass shaft and Teflon stir bar was used to mix the prepolymer while continuing to purge with argon. Using a syringe, redistilled dimethylsulfoxide (7.5 g), which had been stored in a rubber septum-covered container, was transferred into the reaction kettle. The reaction mixture was stirred until the HPMA was completely dissolved (about 15 min). Dabco 33-LV catalyst (Air Products & Chemicals, Inc., Allentown, Pa.) (10 µL) was added to the reaction kettle as a bolus. The reaction mixture was stirred, as above, at room temperature under argon for one week. The reaction was complete after this time as determined by IR (disappearance of NCO absorption band at ~2270 cm$^{-1}$) and GC (no further change in concentration of residual HMPA with time).

EXAMPLE 2

Preparation of pH Sensors

Fluorescein acrylamide, isomer I (10 mg) was dissolved in 250 µL of absolute alcohol. One hundred microliters of this solution was added to 1.0 g of polyurethanemethacrylamide (PUMAM), synthesized in the preceding example. Darocur® 1173 (Ciba-Geigy Corp., Hawthorne, N.Y.) a photoinitiator, (3 µL) and ascorbic acid palmitate (20 mg) were added to the PUMAM/fluorescein acrylamide solution. The mixture was stirred with a glass rod until homogeneous. The homogeneous mixture was placed in an oven at 50° C. for 18 minutes to dissolve the ascorbic acid palmitate. Silanized fibers (plastic-clad glass, obtained from Ensign-Bickford) were dipped into this mixture and removed prior to curing with a medium pressure arc lamp (340±15 nm bandpass; Blackray) so that only a thin film remained on the tip of the fiber. The resulting sensors were found to be pH responsive and linear with respect to pH values in the range of 6.8 to 7.8.

EXAMPLE 3

Synthesis of a High Molecular Weight, Co-macromonomer of Fluorescein Acrylamide, Isomer I and Preparation of pH Sensors Using a clean, dry, metal spatula, 10.0 g (0.0625 equivalents) Hypol® 2002 hydrophilic prepolymer (W. R. Grace & Co., Lexington, Mass.) was transferred from its storage container, which had been purged with argon during and for two minutes after the transfer, to a 50 ml flame-dried reaction kettle. Dried hydroxyethylmethacrylate (HEMA) (2.08 g, 0.0625 equivalents) (Polyscience Corp., Warrington, Pa.) was rapidly added to the reaction kettle and, immediately thereafter, the kettle was purged with argon after replacing and securely clamping the lid in place. A stirrer was used to mix the prepolymer while continuing to purge with argon. Ethyl acetate (10.0 g) and dibutyltin dilaurate (5 µL) catalyst were added, and the reaction mixture was incubated at room temperature for two hours. The mixture was then dried under a stream of nitrogen and a sample of the mixture cured by exposure to a medium pressure arc lamp.

A monomer mixture was then prepared containing 1.5 g of the above-prepared prepolymer, 0.5 g ethanol, 0.005 g fluorescein acrylamide, and 0.099 g Irgacure®-500 (Ciba-Geigy, Hawthorne, N.Y.) photoinitiator. The monomer mixture was grafted onto a silanized glass/plastic fiber and cured with ultraviolet radiation. The pH sensor thus prepared was found to be pH responsive with respect to measurement of pH values in the range of 6.5 to 8.2.

Similar monomer mixtures were then prepared containing 1.5 g of the prepolymer, 0.5 g ethanol, varying amounts of fluorescein acrylamide as indicated in the graph of FIG. 1, and ethylene glycol dimethacrylate (EGDMA) (approximately 0.5 wt. % relative to the prepolymer), to crosslink the polymer. The mixtures were grafted onto silanized glass/plastic fibers as above, and cured with ultraviolet radiation. The effect of dye/polymer ratios on pKa was then evaluated and plotted in FIG. 1.

EXAMPLE 4

Synthesis of Polyurethane Polyethylene Glycol a Hydrophilic Urethane Olefin Prepolymer Using a clean, dry, metal spatula, 11.72 g (0.0183 equivalents) Hypol® 2000 hydrophilic prepolymer (W. R. Grace & Co.) was transferred from its storage container, which had been purged with argon during and for two minutes after the transfer, to a 50 ml flame-dried reaction kettle. Hydroxy-terminated polyethylene glycol 1000 methacrylate (18.28 g; 0.0183 equivalents) (Monomer-Polymer and Dajec Laboratories ["MTM"], Trevose, Pa.) was rapidly added to the reaction kettle and, immediately thereafter, the kettle was purged with argon after replacing and securely clamping the lid. An air stirrer was used to mix the prepolymer while continuing to purge with argon. Using a syringe, distilled dimethylsulfoxide (10.0 g), which had been stored in a rubber septum-covered container, was transferred into the reaction kettle. The reaction mixture was stirred about 15 minutes. Dabco 33-LV catalyst (Air Products & Chemicals, Inc., Allentown, Pa.) (10 µL) was added to the reaction kettle as a bolus. The reaction mixture was stirred, as above, at room temperature under argon for two days. The reaction was complete after this time as determined by IR (disappearance of NCO absorption band at ~2270 cm$^{-1}$). The resulting prepolymer can be used to prepare pH sensors as described in Example 3.

We claim:

1. A fluorescent polymer composition useful in an optical sensor for the measurement of pH in a fluid sample, comprising a copolymer of (a) a water-dispersable urethane olefin precursor containing recurring ether linkages, and (b) a copolymerizable monomeric fluorescent indicator species, wherein the ratio of fluorescent indicator species to urethane olefin precursor in the copolymer is selected to provide the copolymer with an apparent pKa of at least about 6.6 to about 8.0.

2. The fluorescent polymeric composition of claim 1, wherein the ratio of fluorescent indicator species to urethane olefin precursor in the copolymer is selected to provide the copolymer with an apparent pKa in the range of about 7.2 to about 7.8.

3. The fluorescent polymeric composition of claim 1, wherein the ratio of fluorescent indicator species to urethane olefin precursor in the copolymer, in equivalents, is in the range of about 0.001 to about 0.100.

4. The fluorescent polymeric composition of claim 3, wherein the ratio of fluorescent indicator species to urethane olefin precursor in the copolymer, in equivalents, is in the range of about 0.005 to about 0.015.

5. The fluorescent polymeric composition of claim 1, wherein the urethane olefin precursor contains recurring urethane units -O-(CO)-NH-, recurring polyether units

[-CH$_2$)$_n$-O-] where n is an integer in the range of 1 to 6, inclusive, and termini of the general formula -R-(CO)-CR'=CH$_2$, wherein R is O or NH, and R' is H or lower alkyl.

6. The fluorescent polymeric composition of claim 5, wherein the urethane olefin precursor has the structural formula

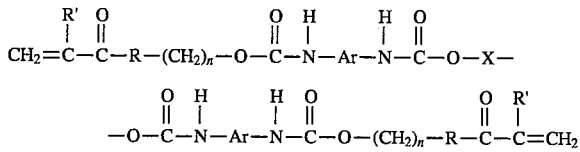

in which:

R is O or NH;

R' is H or lower alkyl;

Ar is a monocyclic aromatic moiety, either unsubstituted or substituted with one to four substituents selected so as not to interfere with polymerization or use of the cured polymer in the pH sensor;

X is a polyether linkage containing approximately 2 to 100 recurring mer units having the structure [-(CH$_2$)$_n$-O-]; and n is an integer in the range of 1 to 6 inclusive.

7. The fluorescent polymeric composition of claim 6, wherein n is 2 or 3.

8. The fluorescent polymeric composition of claim 6, wherein the urethane olefin precursor has a molecular weight in the range of approximately 1,000 to 25,000.

9. The fluorescent polymeric composition of claim 8, wherein the urethane olefin precursor has a molecular weight in the range of approximately 1,800 to approximately 5,000.

10. The fluorescent polymeric composition of claim 9, wherein the urethane olefin precursor has a molecular weight in the range of approximately 1,800 to approximately 2,500.

11. The fluorescent polymeric composition of claim 1, wherein the fluorescent indicator species is selected from the group consisting of fluorescein, carboxyfluorescein, fluorescein acrylamide, fluorescein isothiocyanate, coumarin, seminaphthorhodafluorescein, seminaphthofluorescein, naphthofluorescein, hydroxypyrene trisulfonic acid and dichlorofluorescein, said species modified so as to enable copolymerization with the urethane olefin precursor.

12. The fluorescent polymeric composition of claim 11, wherein the modification comprises incorporation into the fluorescent indicator species of a more reactive moiety selected from the group consisting of acrylate, acrylamide, allyl esters and allyl amides.

13. A fluorescent polymeric composition useful in an optical sensor for the measurement of pH in a fluid sample, comprising a copolymer of (a) a water-dispersable urethane olefin precursor containing recurring ether linkages and having the structural formula

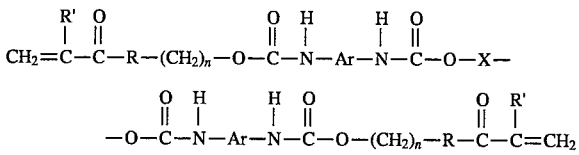

wherein R is O or NH, R' is H or lower alkyl, Ar is a monocyclic aromatic moiety, either unsubstituted or substituted with one to four substituents selected so as not to interfere with polymerization or use of the cured polymer in the pH sensor, X is a polyether linkage containing approximately 2 to 100 recurring mer units having the structure [-(CH$_2$)$_n$-O-], and n is an integer in the range of 1 to 6, inclusive, and (b) a copolymerizable, monomeric fluorescent indicator species selected from the group consisting of fluorescein, carboxyfluorescein, fluorescein acrylamide, fluorescein isothiocyanate, coumarin, seminaphthorhodafluorescein, seminaphthofluorescein, naphthofluorescein, hydroxypyrene trisulfonic acid and dichlorofluorescein, said species modified so as to enable copolymerization with the urethane olefin precursor, wherein the ratio of fluorescent indicator species to urethane olefin precursor, in equivalents, is in the range of about 0.001 to about 0.100.

* * * * *